United States Patent [19]

Sirkar

[11] Patent Number: 4,921,612
[45] Date of Patent: May 1, 1990

[54] ASYMMETRICALLY-WETTABLE POROUS MEMBRANE PROCESS

[75] Inventor: Kamalesh K. Sirkar, Scotch Plains, N.J.

[73] Assignee: The Trustees of Stevens Institute of Technology, Hoboken, N.J.

[21] Appl. No.: 208,869

[22] Filed: Jun. 15, 1988

Related U.S. Application Data

[63] Continuation of Ser. No. 789,992, Oct. 22, 1985, abandoned.

[51] Int. Cl.$^5$ .................... B01D 11/04; B01D 13/00; B01D 13/01; C12N 11/04
[52] U.S. Cl. .................... 210/644; 210/634; 210/500.21; 210/500.23; 435/182
[58] Field of Search .................... 55/16; 435/180, 182, 435/288; 210/500.21, 500.23, 644, 645, 634

[56] References Cited

U.S. PATENT DOCUMENTS

| | | | |
|---|---|---|---|
| 2,365,457 | 12/1944 | Daniel | 210/637 |
| 3,244,763 | 4/1966 | Cahn | 260/677 |
| 3,396,510 | 8/1968 | Ward, III et al. | 55/16 |
| 3,422,008 | 1/1969 | McLain | 55/16 X |
| 3,447,286 | 6/1969 | Dounoucos | 55/16 |
| 3,556,990 | 1/1971 | Gulko | 208/290 |
| 3,676,220 | 7/1972 | Ward, III | 55/158 X |
| 3,719,590 | 3/1973 | Li et al. | 208/308 |
| 3,770,842 | 11/1973 | Steigelmann et al. | 55/16 X |
| 3,799,873 | 3/1974 | Brown | 210/641 |
| 3,800,506 | 4/1974 | Hughes et al. | 55/16 |
| 3,823,529 | 7/1974 | Hughes et al. | 55/16 |
| 3,911,080 | 10/1975 | Mehl et al. | 55/16 X |
| 3,917,526 | 11/1975 | Jennings | 210/641 |
| 3,925,037 | 12/1975 | Ward, III et al. | 55/158 |
| 3,951,789 | 4/1976 | Lee et al. | 210/644 |
| 3,956,112 | 5/1976 | Lee et al. | 210/644 |
| 3,957,504 | 5/1976 | Ho et al. | 75/101 |
| 3,980,605 | 9/1976 | Steigelmann et al. | 55/16 X |
| 4,000,065 | 12/1976 | Ladha et al. | 210/652 |
| 4,005,012 | 1/1977 | Wrasidlo | 210/654 |
| 4,014,665 | 3/1977 | Steigelmann | 55/16 |
| 4,015,955 | 4/1977 | Steigelmann et al. | 55/16 |

(List continued on next page.)

OTHER PUBLICATIONS

Lee et al., A.I.Ch.E. Journal, vol. 24, pp. 860–868, (Sep. 1978).
Kan and Shuler, Biotechnology and Bioengineering, vol. 20, pp. 217–230, (1978).
Webster and Shuler, Biotechnology and Bioengineering, vol. 20, pp. 1541–1556, (1978).
Kimura et al., Recent Developments in Separation Science, (CRC Press, Cleveland, Ohio, 1978).
Travenol Laboratories, Inc., "Travenol TMO Membrane Oxygenator", product brochure, (Jan. 1979).
Kimura and Walmet, Separation Science and Technology, vol. 15, pp. 1115–1133, (1980).
Chemical Engineering, Oct. 17, 1983, pp. 14, 17.
Kim, Presentation at AICHE Summer National Meeting, Denver, Colo., (Aug. 29, 1983).
Webster, American Biotechnology Laboratories, pp. 29–35, (Dec. 1983).
Chemical Week, Jun. 27, 1984, p. 96.
Chemical and Engineering News, vol. 62, p. 33, (Jun. 25, 1984).
Travenol Laboratories, Inc., "5M1430 TMO Total Bypass Membrane Oxygenator—Adult", product brochure, (Feb. 1978).

Primary Examiner—W. Gary Jones
Attorney, Agent, or Firm—Pennie & Edmonds

[57] ABSTRACT

An asymmetrically-wettable, porous membrane has a hydrophilic side and a hydrophobic side. The membrane has pores which pass through the membrane to provide communication between the hydrophilic side and the hydrophobic side. The membrane can be used in a process for transferring a solute from a liquid feed solution to a liquid extractant which is substantially immiscible with the feed solution. The process comprises contacting the hydrophilic side of the membrane with one solution and contacting the hydrophobic side of the membrane with the other solution. The interface between the feed solution and the extractant is substantially immobilized at the porous membrane. Solute is transferred from the feed solution to the extractant through the pores of the membrane.

11 Claims, 3 Drawing Sheets

U.S. PATENT DOCUMENTS

| | | | |
|---|---|---|---|
| 4,062,882 | 12/1977 | Gupta | 260/428.5 |
| 4,106,920 | 8/1978 | Hughes et al. | 55/16 X |
| 4,115,514 | 9/1978 | Ward III | 55/16 X |
| 4,117,079 | 9/1978 | Bellows | 55/16 X |
| 4,119,408 | 10/1978 | Matson | 55/16 X |
| 4,147,754 | 4/1979 | Ward, III | 55/16 X |
| 4,174,374 | 11/1979 | Matson | 55/16 X |
| 4,187,086 | 2/1980 | Walmet et al. | 55/16 |
| 4,198,293 | 4/1980 | Ogawa et al. | 210/636 |
| 4,214,020 | 7/1980 | Ward et al. | 210/500.23 |
| 4,220,535 | 9/1980 | Leonard | 210/321 |
| 4,235,983 | 11/1980 | Steigelmann et al. | 55/16 X |
| 4,239,506 | 12/1980 | Steigelmann et al. | 55/16 |
| 4,296,205 | 10/1981 | Verma | 210/644 X |
| 4,303,068 | 12/1981 | Zelman | 210/646 X |
| 4,306,946 | 12/1981 | Kim | 204/51 |
| 4,326,960 | 4/1982 | Iwahori et al. | 210/650 |
| 4,329,224 | 5/1982 | Kim | 210/709 |
| 4,353,799 | 10/1982 | Leonard | 210/321.3 |
| 4,366,063 | 12/1982 | O'Connor | 210/652 |
| 4,392,960 | 7/1983 | Kraus et al. | 210/651 |
| 4,406,752 | 9/1983 | Weininger et al. | 204/3 |
| 4,418,148 | 11/1983 | Oberhardt | 435/182 X |
| 4,420,398 | 12/1983 | Castino | 210/645 X |
| 4,443,414 | 4/1984 | Kim | 423/54 |
| 4,445,990 | 5/1984 | Kim et al. | 204/151 |
| 4,455,236 | 6/1984 | Kim | 210/721 |
| 4,516,984 | 5/1985 | Warner et al. | 55/16 |
| 4,554,069 | 11/1985 | Aid et al. | 210/101 |
| 4,789,468 | 12/1988 | Sirkar | 210/137 |
| 4,816,407 | 3/1989 | Matson | 210/644 |

ASYMMETRICALLY-WETTABLE POROUS MEMBRANE PROCESS

This is a continuation of application Ser. No. 789,992, filed Oct. 22, 1985, now abandoned.

TECHNICAL FIELD

The present invention relates to a porous membrane and to a membrane process for transferring solute from a liquid feed solution to a liquid extractant which is substantially immiscible with the feed solution.

BACKGROUND ART

In chemical processes liquid-liquid extractions are often used to transfer a solute dissolved in a first liquid to a second liquid which is essentially immiscible with the first liquid. The solution of the solute in the first liquid is generally termed a feed solution and the second liquid is generally termed an extractant. In an undissolved state the solute can be a solid, a liquid, or a gas. The solute tends to distribute itself between the two liquids in accordance with the relative solubility of the solute in the two liquids when the feed solution is brought into contact with the liquid extractant. Since they are essentially immiscible, the feed solution and the liquid extractant form two distinct thermodynamic phases when in contact with one another. These two phases can be physically separated from one another, which effects a separation of a fraction of the solute from the feed solution.

Typically in conventional liquid-liquid extraction processes to promote a rapid distribution of the solute between a feed solution and an extractant, the feed solution and the extractant are mixed together intimately. Frequently, however, such intimate mixing gives rise to troublesome problems. For example, the mixing generally involves forming a dispersion of one of the liquids in the other. The resulting dispersion is frequently quite stable, so that it takes a long time for the dispersed liquid to coalesce. Consequently, the throughput of the solute-transfer process is undesirably low or the inventory of feed solution and extractant tied up in the process is undesirably high.

U.S. Pat. No. 3,956,112 to Lee et al. refers to an extraction process in which a porous membrane serves as a partition between two immiscible solvents. Solutes from one solvent are transferred to the other solvent by way of the porous membrane via direct solvent-solvent contact. In practice, however, conventional extraction processes in which immiscible solvents are separated by a porous membrane generally do not prevent one solvent from forming a dispersion in the other. One or the other solvent typically seeps through the porous membrane and becomes dispersed in the solvent on the other side of the membrane. Consequently, conventional extraction processes involving immiscible solvents separated by a porous membrane generally must provide a settling tank and a solvent return mechanism to coalesce the dispersion formed by the seepage of one of the solvents through the membrane and to return the solvent so recovered to its source.

In my U.S. patent application Ser. No. 644,895, filed Aug. 28, 1984 (the '895 application), now U.S. Pat. No. 4,789,468, I disclosed a solute transfer process in which a first side of a porous membrane is contacted with a feed solution and a second, opposing side of the membrane is contacted with a liquid extractant which is substantially immiscible with the feed solution. On the surface of the porous membrane either the feed solution tends to displace the extractant, or vice versa. The liquid which tends to displace the other defines a membrane-wetting liquid. The process of the '895 application further includes the step of maintaining a pressure difference across the membrane between the feed solution and the extractant. The pressure difference is imposed in a direction and a magnitude which is effective substantially to prevent the membrane-wetting liquid from flowing through the membrane and dispersing in the liquid on the other side. The interface between the feed solution and the extractant is thereby effectively immobilized at the porous membrane. The feed solution and the extractant come into contact through the pores of the membrane, permitting solute to be transferred through the pores from the feed solution to the extractant.

Although the solute-transfer process of the '895 application has proven satisfactory for many applications, there is room for improvement. In general the process requires a pressure-difference controller for maintaining a pressure difference across a porous membrane within a predetermined range to immobilize the interface between the feed solution and the extractant at the membrane. Suitable pressure-difference controllers tend to be expensive and prone to malfunction. Failure of the pressure difference controller to maintain the pressure difference in a required range generally results in seepage of the membrane-wetting liquid through the membrane. Such seepage generally results in a loss of the membrane-wetting liquid and concomittant contamination of the liquid separated from the membrane-wetting liquid by the membrane.

DISCLOSURE OF THE INVENTION

I have invented an asymmetrically-wettable, porous membrane and a process for transferring solute from a liquid feed solution to a liquid extractant which avoids problems of the prior art noted above.

Broadly, the asymmetrically-wettable, porous membrane of the invention has one side which is hydrophilic and an opposing side which is hydrophobic. The membrane has pores which pass through the membrane to provide communication between the hydrophilic side and the hydrophobic side.

The process of the invention is suitable for transferring solute from a liquid feed solution to a liquid extractant when the feed solution and the extractant are substantially immiscible with one another when in direct contact. One of the feed solution and the extractant is substantially miscible with water and defines a water-miscible liquid. The other of the feed solution and the extractant is substantially immiscible with water and defines a water-immiscible liquid. The process of the invention involves contacting the hydrophilic side of an asymmetrically-wettable, porous membrane of the invention with the water-miscible liquid. The process further includes the step of contacting the hydrophobic side of the membrane with the water-immiscible liquid. The feed solution and the extractant can thereby come in contact through the pores of the membrane, permitting solute to be transferred through the pores from the feed solution to the extractant. The interface between the feed solution and the extractant is substantially immobilized at the porous membrane.

Preferred processes of the invention require a smaller pressure difference across the asymmetrically-wettable porous membrane to immobilize the interface between a feed solution and an extractant at the membrane than is required to immobilize the interface at a generally corresponding membrane having identical surface wetting properties on each side. More preferably, the interface can be immobilized in preferred processes of the invention with the pressure of the liquid on one side of the membrane approximately equal to the pressure of the liquid on the opposing side. In other words, even a pressure difference of approximately zero across the membrane preferably results in immobilization of the interface between the feed solution and the extractant at the membrane. It is most preferable for the interface between a feed solution and a liquid extractant to be immobilized at a membrane of the invention for a range of pressure differences across the membrane, the range including positive and negative pressure differences as well as zero pressure difference.

The range of differences in pressure effective to immobilize the interface between a particular feed solution and extractant at a particular asymmetrically-wettable porous membrane depends upon a number of factors, including the relative tendency of the feed solution and the extractant to wet both sides of the membrane. Other factors include the interfacial tension between the feed solution and the extractant, flow characteristics cf each liquid at the surface of the membrane and the effective diameters of the pores of the membrane. Values of the maximum pressure difference in a given direction across an asymmetrically-wettable, porous membrane effective to immobilize the interface between the feed solution and the extractant at the membrane cannot in general be predicted a priori. Such a maximum pressure difference is referred to as a "breakthrough pressure." Because of the number of factors involved, it is preferred to establish experimentally for a particular asymmetrically-wettable, porous membrane; feed solution; and extractant a range of interface-immobilizing pressure differences from a breakthrough pressure in one direction across the membrane to a breakthrough pressure in the opposite direction across the membrane. Ordinarily, for a given feed solution and extractant, it is most preferable to adjust the wetting characteristics of the two sides of the asymmetrically-wettable, porous membrane so that a range of pressure differences which serves to immobilize the interface between the feed solution and the extractant varies from a breakthrough pressure in a first direction across the membrane to a breakthrough pressure in a second, opposing direction which approximately equals the value of the breakthrough pressure in the first direction.

Preferred asymmetrically-wettable, porous membranes of the invention can be made by a number of methods.

For example, an asymmetrically-wettable, porous membrane of the invention can be prepared from a first membrane outer layer composed of a porous hydrophilic material and a second membrane outer layer composed of a porous hydrophobic material to form a composite structure. Preferred materials for the hydrophilic membrane outer layer of laminer composite asymmetrically-wettable, porous membranes include porous regenerated cellulose, porous cellulose acetate, porous cellulose acetate-nitrate, porous cellulose triacetate, microporous glass, and porous procelain. Preferred materials for the hydrophobic membrane outer layer of laminer composite asymmetrically-wettable, porous membranes include porous polyethylene, porous polypropylene, and porous polytetrafluoroethylene (PTFE). For many applications a suitable asymmetrically-wettable, porous membrane can be formed by placing a film of a porous hydrophilic material and a film of a porous hydrophobic material side by side and clamping or otherwise mechanically urging the two films together. Alternatively, a film of porous hydrophilic material and a film of a porous hydrophobic material can be bonded together adhesively, provided that the adhesive does not block too large a portion of the pores which pass through the resulting membrane. Two-layer composite asymmetrically-wettable, porous membranes can be formed by extrusion.

A layer of a first porous material can be cast upon a film of a second porous material cf opposite wetting characteristics to form an asymmetrically-wettable, porous membrane. For example, a solution of cellulose acetate in acetone can be spread upon a film of porous polypropylene and the resulting film immersed in cold water to remove the acetone and gel the cellulose acetate into a porous membrane layer. If desired, the cellulose acetate layer can then be deacetylated to form a layer of porous regenerated cellulose on the film of porous polypropylene. Regenerated cellulose generally has a greater solvent resistance than cellulose acetate. In the case of hollow fibers, a hollow fiber of a first porous polymer can be drawn through a solution of a second polymer to deposit a coating of the solution of the second polymer on the outside of the fiber. The solvent can then be removed under conditions which leave a porous layer of the second polymer on the fiber. For example, a layer of porous cellulose acetate can be cast upon hollow fibers of porous polypropylene by drawing the polypropylene fibers first through a solution of cellulose acetate in acetone and then through a bath of cold water.

A porous layer of a first polymer can be grafted upon a porous film of a second polymer in which one polymer is hydrophilic and the other polymer is hydrophobic. Such a grafting process can be carried out in many cases by coating one side of the film of the second polymer with a monomer of the first polymer, possibly including a diluent, and then exposing the coated side to ultraviolet radiation to polymerize the monomer to form the first polymer. Removal of the diluent, if present, can enhance the formulation of pores in the first polymer.

A porous film can be treated on one surface to alter the wettability characteristics of the surface. For example, one side of a hydrophobic film of porous polyethylene, porous polypropylene, or porous polytetrafluoroethylene can be treated to render the side less hydrophobic or even hydrophilic. Such treatments can include exposure to an agent which tends to render the surface hydrophilic. Examples of such agents include chromic acid, concentrated sulfuric acid or a powerful oxidizing agent. Alternatively, one surface of the film can be exposed to a corona discharge or other ion or free radical discharge.

The effective diameters of the pores of the asymmetrically-wettable, porous membrane of the invention preferably lie in the range of from about 1nm to about $10^{-2}$ mm. Preferably, the pores of a given membrane should be approximately uniform in size. The porous membrane should be as thin as is consistent with the need to be strong enough to withstand any pressure difference applied across the membrane. Porous membranes from about 25 $\mu$m to about 125 $\mu$m in thickness are preferred. Certain feed solutions or extractants may cause certain membrane materials to swell. Such swelling generally causes no harm as long as the swollen membrane remains sufficiently strong.

For solute-transfer processes carried out on an industrial scale, it is preferred to employ hollow tubular fibers with asymmetrically-wettable, porous walls. Bundles of large numbers of such tubular fibers can provide a high value for the ratio of the area of porous membrane through which the solute transfer occurs to the volume of the vessel which contains the feed-solution/-membrane/extractant system.

When a liquid is caused to flow through a hollow tubular fiber, a significant pressure drop can occur between the inlet and outlet ends of the fiber. Care should be taken to ensure that any pressure difference across the porous wall of a hollow tubular fiber remains less than the breakthrough pressure along the entire length of the fiber for the higher-pressure liquid with respect to the membrane material which it does not wet.

A preferred membrane solute transfer unit for carrying out solute-transfer processes of the invention includes an asymmetrically-wettable, porous membrane located within a liquid-tight housing. The membrane divides the interior of the housing into two chambers: a feed solution chamber and an extractant chamber. The membrane is oriented so that the side of the membrane which tends to be preferentially wetted by the feed solution faces the feed-solution chamber and the opposing side of the membrane which tends to be preferentially wetted by the extractant faces the extractant chamber. Pores of the membrane provide communication between the two chambers. The housing is provided with inlet and outlet ports which permit feed solution to be introduced and discharged from the feed solution chamber and liquid extractant to be introduced and discharged from the extractant chamber.

The present invention permits two or more solute-transfer processes to be carried out conveniently at the same time in a single vessel. For example, a preferred double-transfer solute-transfer unit includes a liquid-tight housing, the interior of which is divided by two asymmetrically-wettable, porous membranes into a sequence of three side-by-side chambers. A feed solution could be pumped through a first end chamber. An intermediate chamber separated from the first end chamber by a first asymmetrically-wettable, porous membrane could contain an intermediate extractant liquid substantially immiscible with the feed solution. A second end chamber separated from the intermediate chamber by a second asymmetrically-wettable, porous membrane could have pumped through it a back-extractant liquid which is immiscible with the intermediate extractant. The back-extractant liquid could be completely miscible with the feed solution, if desired. In the case of such a feed solution/intermediate extractant/back extractant process, the first membrane is oriented so that the side of the membrane which tends to be preferentially wetted by the feed solution faces the first end chamber and the opposing side which tends to be preferentially wetted by the intermediate extractant faces the intermediate chamber. The second membrane is oriented so that the side of the membrane which is preferentially wetted by the back-extractant liquid faces the second end chamber and the opposing side of the membrane which tends to be preferentially wetted by the intermediate extractant faces the intermediate chamber. Solute in the feed solution in the first chamber could be transferred to the intermediate extractant in the intermediate chamber through the first porous membrane. The solute could then diffuse through the intermediate extractant to the second porous membrane and then be transferred to the back extractant through the second membrane. The intermediate chamber preferably is as narrow as practical to minimize the diffusion path length and to minimize the inventory of intermediate extractant and solute held up in the intermediate extractant. If required a first interface-immobilizing pressure difference could be maintained across the first membrane to oppose any tendency of the feed solution or the intermediate extractant, as the case may be, to pass through the membrane. Similarly, if required, a second interface-immobilizing pressure difference could be maintained across the second membrane to oppose any tendency of the intermediate extractant or the back extractant, as the case may be, to pass through the membrane. Preferably, no interface-immobilizing pressure difference is required.

Alternatively, a feed solution could be pumped through the intermediate chamber of the preferred double-transfer solute-transfer unit discussed in the preceding paragraph. First and second extractant liquids, each immiscible with the feed solution, could be pumped through the first and second end chambers, respectively. In the case of such a first extractant/feed solution/second extractant process, the first membrane is oriented so that the side of the membrane which tends to be preferentially wetted by the first extractant faces the first end chamber and the opposing side which tends to be preferentially wetted by the feed solution faces the intermediate chamber. The second membrane is oriented so that the side of the membrane which tends to be preferentially wetted by the second extractant faces the second end chamber and the opposing side of the membrane which tends to be preferentially wetted by the feed solution faces the intermediate chamber. If required, an interface-immobilizing pressure difference could then be maintained across each of the first and the second porous membrane to oppose the tendency of one or the other of the feed solution or extractant liquid to pass through the membrane. By using two different extractant liquids, two different solutes could be extracted from a single feed solution at the same time.

For industrial scale solute-transfer processes, particularly processes involving two or more simultaneous solute transfers, it is preferred to employ a plurality of bundles of hollow tubular fibers with asymmetrically-wettable, porous walls. For example, in the case of a process involving a solute transferred from a feed solution to a back extractant by way of an intermediate extractant which is substantially immiscible with both the feed solution and the back extractant, a preferred double-transfer extraction cell includes two bundles of hollow tubular fibers with asymmetrically-wettable porous walls passing through the interior of a liquid-tight housing. The feed solution is pumped through the first bundle of tubular fibers and the back extractant is pumped through the second bundle of tubular fibers. The intermediate extractant fills the interior of the housing, exterior of the tubular fibers. The fibers of the two bundles are preferably commingled and located close to one another to reduce the diffusion path length from the fibers containing the feed solution to the fibers containing the back extractant.

The asymmetrically-wettable, porous membrane of the invention is believed to immobilize the interface between substantially immiscible liquids such as an organic liquid and an aqueous solution by the following mechanism. When an organic liquid contacts the hydrophobic side of the membrane, it enters the pores opening on the hydrophobic side since it wets the hydrophobic side. However, as the organic liquid penetrates further into the pores, it encounters the hydrophilic section of the membrane which it does not wet and therefore does not penetrate. Consequently, pressure need not be applied from the hydrophilic side of the membrane to prevent the organic liquid from seeping through the membrane. On the other hand, an aqueous solution contacting the hydrophilic side of the membrane wets the hydrophilic side of the membrane and enters the pores opening on that side. As it tries to penetrate further into the pores, the aqueous solution encounters the hydrophobic section of the membrane which it does not wet and therefore does not penetrate. Consequently, pressure need not be applied from the hydrophobic side of the membrane to prevent the aqueous liquid from seeping through the membrane. Thus, inside the membrane at an interface between the hydrophobic and the hydrophilic sections of the membrane, an interface tends to form between the aqueous and the organic liquids. This interface between the two substantially immiscible liquids tends to be immobilized at the hydrophobic-hydrophilic interface inside the membrane even when both the immiscible liquids have substantially the same pressure. One or more solutes can be transferred from one liquid to the other across the immobilized interface.

If it is required that the pressure of a liquid on one side of an asymmetrically-wettable, porous membrane of the invention be higher than the pressure of the liquid on the other side, the membrane can generally accommodate the pressure difference provided the pressure difference is not so high as to cause a breakthrough of the higher pressure liquid through the section of the membrane that it does not wet. For example, consider a composite membrane made up of a microporous, hydrophilic cellulose acetate film and a microporous, hydrophobic polypropylene film used for extracting acetic acid from water into xylene. If xylene in contact with the hydrophobic film is to be at a higher pressure than the aqueous acetic acid solution in contact with the cellulose acetate film, then the excess xylene pressure must be less than that needed for xylene to break through the hydrophilic cellulose acetate film containing the aqueous solution in its pores. Correspondingly, if the aqueous solution is to have a higher pressure, then the excess pressure must be less than that needed for the aqueous phase to break through the hydrophobic polypropylene film containing the xylene in its pores.

It is expected that the solute-transfer process of the invention will have wide utility in the chemical and pharmaceutical industries. In fermentation processes, for example, fermentation products can be continuously withdrawn from an aqueous fermentation broth as the fermentation proceeds by transfer of the products to an organic solvent which is immiscible with water. Ethyl alcohol could be extracted from such a broth by a solvent such as dibutyl phthalate or tributyl phosphate separated from the broth by a composite two-layer membrane of porous polypropylene and regenerated cellulose. When an asymmetrically-wettable, porous membrane in hollow fiber form is used for fermentation-extraction applications, it is preferable that the hydrophilic side of the membrane be exposed to the fermentation broth. Cellular debris and other particulate matter in the broth would be prevented from contaminating the solvent stream by the porous membrane. Moreover, either enzymes or whole cells can be immobilized on the porous hydrophilic side of the membrane. For a fermentation-extraction system using hollow fibers of the invention having walls of a composite, layered structure with an inner layer of porous hydrophobic material and an outer layer of porous hydrophilic material, enzymes or whole cells can be immobilized in the porous hydrophilic outer layers. In such a system, an aqueous fermentation broth may flow exterior of the fibers with the broth penetrating the pores of the hydrophilic outer layers, while an organic extractant flows through the lumena of the hollow fibers and wets only the hydrophobic inner layers of the fiber walls. Any fermentation product produced by the immobilized enzymes or cells in the hydrophilic outer layers of the fiber walls will be extracted by the organic solvent in the pores in the hydrophobic inner layers of the fiber walls into the solvent flowing through the lumena of the fibers. Thus cell or enzyme immobilization independent of immobilization in the hydrophilic outer layers of the wals of the hollow fibers is not necessary. In addition, the buildup of the fermentation product—which is often toxic to the microorganism—is generally eliminated. Moreover, the breakdown of fermentation products in the fermentation broth, which is sometimes encountered in conventional fermentation systems, is reduced. Antibiotics or other fermentation products could be extracted from the broth with appropriate extractant liquids. Oxygen could be introduced into and carbon dioxide withdrawn from the fermentation broth using a gas-permeable membrane at the same time as fermentation products were being extracted using the process of the invention. Alternatively, gases could be removed from the fermentation broth using a liquid extractant flowing through porous hollow fibers of the invention.

The process of the invention could also be used to separate phenol from waste water using MIBK or diisopropyl either as an extractant. If the waste water contained hydrogen sulfide or ammonia in addition to phenol, the MIBK or diisopropylether extractant could be used to extract the phenol, and the hydrogen sulfide or ammonia could be removed simultaneously using a gas-permeable membrane. Aromatics could be extracted from petroleum distillates using sulfolane or propylene carbonate as an extractant. Toluene could be extracted from n-heptane using an intermediate extractant of an aqueous solution of cuprous ammonium acetate. The toluene could in turn be extracted from the cuprous ammonium acetate solution with a back extractant of kerosene. Finally, the toluene could be removed from the kerosene using a simple flash distillation. Separation of toluene from n-heptane is difficult to accomplish by distillation alone. Copper can be extracted from a dilute aqueous solution into a substantially immiscible liquid organic solvent containing a liquid ion-exchanger. Other applications of the solute-transfer process of the invention will occur to persons skilled in the art.

BRIEF DESCRIPTION OF THE DRAWINGS

Preferred embodiments of the invention are described below with reference to the following figures.

BEST MODE FOR CARRYING OUT THE INVENTION

Figure 1:
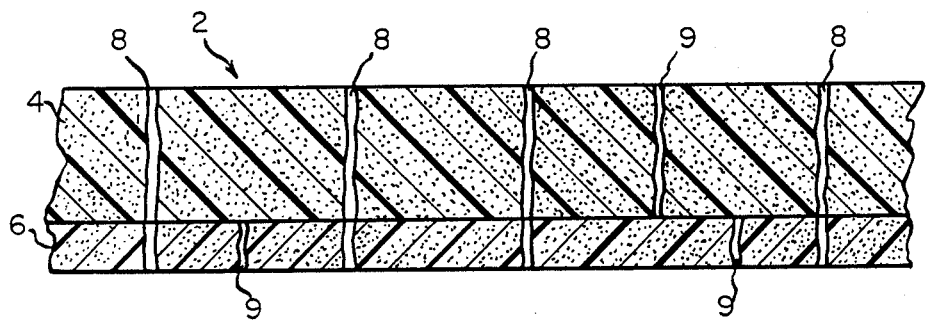
FIG. 1 is a cross-sectional schematic diagram of an asymmetrically wettable, porous membrane of the invention.

Turning now to FIG. 1, an asymmetrically-wettable, porous membrane 2 has a hydrophilic layer 4 and a hydrophobic layer 6. Both the hydrophobic layer 6 and the hydrophilic layer 4 are separately porous. A fraction of the pores 8 extend completely through the membrane 2 and provide communication from one side of the membrane to the other. A fraction of the pores 9 terminate at the junction between the hydrophobic layer 6 and the hydrophilic layer 4. For simplicity, only a relative few of each type of pores are illustrated in FIG. 1.

Figure 2:
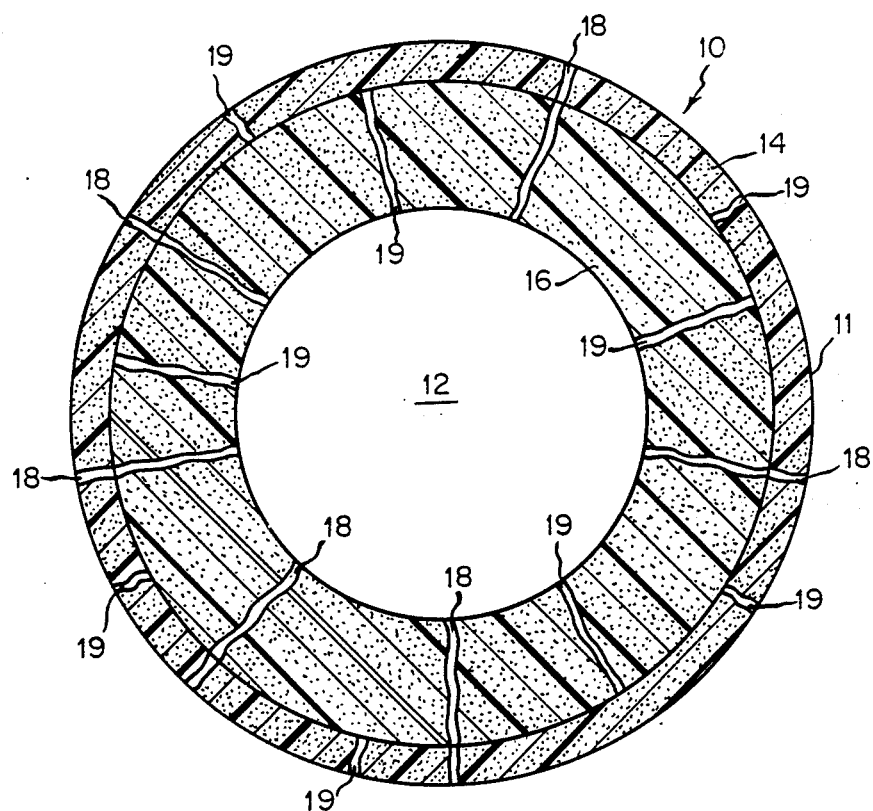
FIG. 2 is a cross-sectional schematic diagram of a hollow fiber of the invention having an asymmetrically-wettable, porous wall.

Turning now to FIG. 2, a hollow fiber 10 has a tubular wall 11 and a lumen 12 which extends axially through the fiber. The tubular wall 11 has a radially outer hydrophilic layer 14 and radial inner hydrophobic layer 16. Thus the wall 11 of the hollow fiber 10 is an asymmetrically-wettable, porous membrane generally similar to the membrane illustrated in FIG. 1. As in the case of the membrane of FIG. 1, the tubular wall 11 has a fraction of pores 18 which extend entirely through the wall. The pores 18 provide communication between the lumen 12 of the hollow fiber and the space surrounding the radially outer surface of the fiber. A fraction of the pores 19 do not extend entirely through the tubular wall 11 of the hollow fiber 10.

Figure 3:
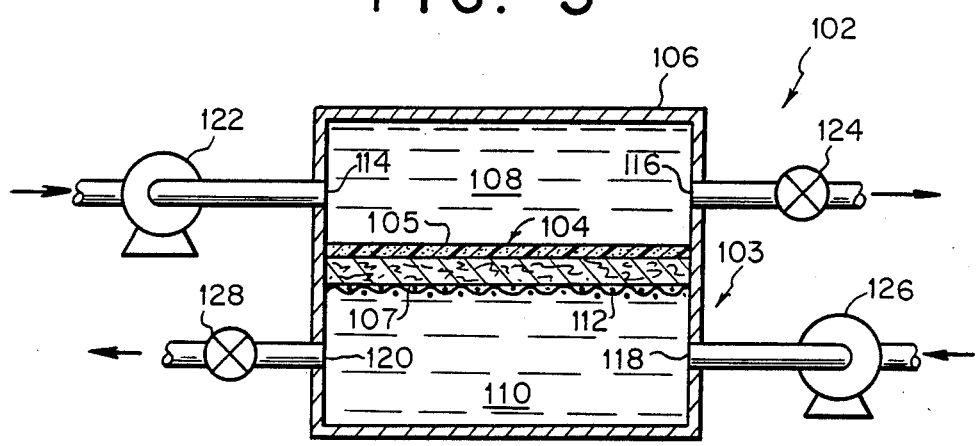
FIG. 3 is a schematic diagram of a first solute-transfer unit which employs an asymmetrically wettable, porous membrane of the invention.

Turning now to FIG. 3, a membrane solute-transfer unit 102 includes an extraction cell 103 which has an asymmetrically-wettable, porous membrane 104 located within a housing 106. The membrane 104 is sealed to the walls of the housing 106 and divides the interior of the housing into a feed solution chamber 108 and a liquid extractant chamber 110. A side 105 of the membrane 104 facing the feed solution chamber 108 is hydrophilic. An opposing side 107 of the membrane 104 which faces the liquid extractant chamber 110 is hydrophobic. Pores passing through the membrane 104 provide communication between the feed solution chamber 108 and the extractant chamber 110. A reinforcing screen 112 is adjacent to the porous membrane 104 on the side of the membrane facing the extractant chamber 110. The screen 112 provides mechanical support for the membrane 104.

A feed-solution inlet port 114 and a feed-solution outlet port 116 permit a feed solution to be introduced into and discharged from the feed solution chamber 108. A feed-solution pump 122 is connected to the feed-solution inlet port 114 and is capable of pumping feed solution at a substantially constant rate under pressure into the feed solution chamber 108. A feed solution discharge throttle valve 124 is connected to the feed-solution outlet port 116 for controlling the liquid pressure of the feed solution flowing through the feed-solution chamber 108.

An extractant inlet port 118 and an extractant outlet port 120 permit a liquid extractant to be introduced into and discharged from the extractant chamber 110. An extractant pump 126 is connected to the extractant inlet port 118 and is capable of pumping the liquid extractant through the extractant chamber 110 at a substantially constant rate. An extractant discharge throttle valve 128 is connected to the extractant outlet port 120 for controlling the liquid pressure of the extractant flowing through the extractant chamber 110.

In operation, an aqueous feed solution is pumped by the feed solution pump, 22 through the feed-solution chamber 108 at a substantially constant rate. A water-immiscible extractant is pumped by the extractant pump 126 through the extractant chamber 110 at a substantially constant rate. The liquid pressure in the feed-solution chamber 108 is approximately the same as the liquid pressure in the extractant chamber 110. The aqueous feed solution wets the hydrophilic side 105 of the asymmetrically-wettable, porous membrane 104. The non-aqueous extractant wets the hydrophobic side 107 of the membrane 104. Solute from the feed solution is transferred through the pores of the membrane 104 to the extractant. The interface between the aqueous feed solution and the water-immiscible extractant is essentially immobilized at the membrane 104.

Figure 4:
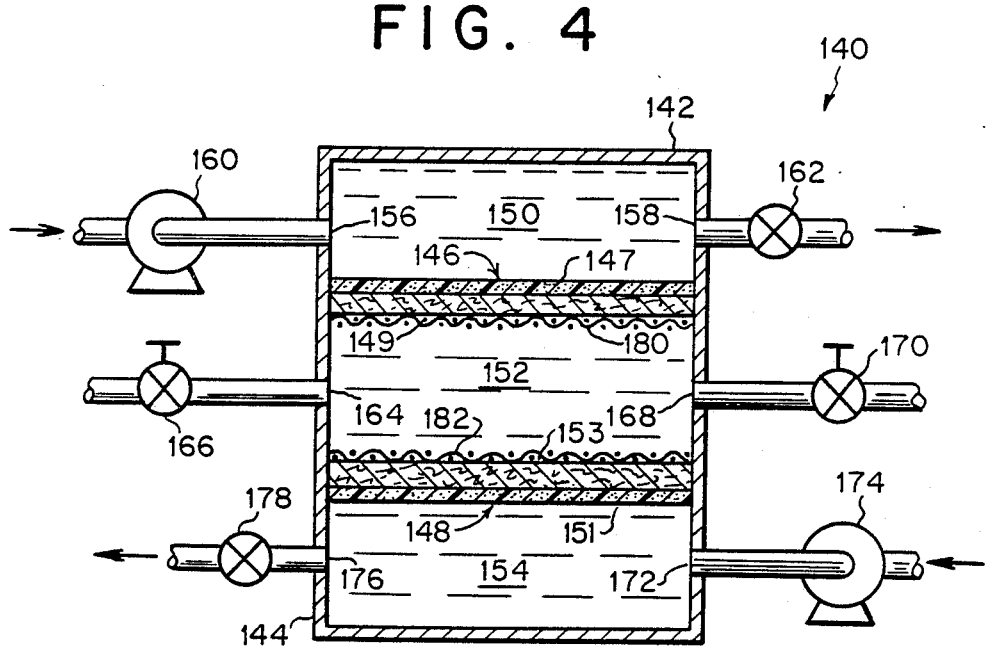
FIG. 4 is a schematic diagram of a second solute-transfer unit which employs two asymmetrically-wettable, porous membranes of the invention.

Turning now to FIG. 4, a membrane solute-transfer unit 140 has a three-chamber extraction cell 142. The extraction cell 142 has a housing 144 and a first and a second asymmetrically-wettable, porous membrane 146 and 148 located within the interior of the housing 144. The first and the second membranes 146 and 148 are sealed to the housing 144 and divide the housing into three chambers: a feed solution chamber 150, an intermediate-extractant chamber 152, and a back-extractant chamber 154. The intermediate-extractant chamber 152 is located between the feed-solution chamber 150 and the back-extractant chamber 154. Pores in the first porous membrane 146 provide communication between the feed-solution chamber 150 and the intermediate-extractant chamber 152; pores in the second porous membrane 148 provide communication between the back-extractant chamber 154 and the intermediate-extractant chamber 152. A first side 147 of the first membrane 146 facing the feed solution chamber 150 is hydrophilic; an opposing side 149 of the first membrane 146 is hydrophobic. A first side 151 of the second membrane 148 facing the back-extractant chamber 154 is hydrophilic; an opposing side 153 of the second membrane 148 is hydrophobic.

The extraction cell housing 144 has a feed-solution inlet port 156 and a feed-solution outlet port 158 for respectively introducing an aqueous feed solution into and discharging the feed solution from the feed solution chamber 150. A feed-solution input pump 160 is connected to the feed solution inlet port 156 and a feed-solution throttle valve 162 is connected to the feed solution discharge port 158. The extraction cell housing 144 has an intermediate-extractant inlet port 164 to which an intermediate-extractant inlet valve 166 is connected for introducing a water-immiscible intermediate extractant into the intermediate extractant chamber 152. The extractant cell housing 144 also includes an intermediate extractant outlet port 168 to which an intermediate-extractant outlet valve 170 is connected for discharging the intermediate extractant from the intermediate extractant chamber 152. The extractant cell housing 144 also has a back-extractant inlet port 172 to which a back-extractant inlet pump 174 is connected and a back extractant outlet port 176 to which a back-extractant discharge throttle valve 178 is connected for pumping an aqueous back extractant through the back-extractant chamber 154.

A first reinforcing screen 180 is located in the extractant cell housing 144 adjacent to the first porous membrane 146 facing the intermediate extractant chamber 152. A second reinforcing screen 182 is located in the extractant-cell housing 144 adjacent to the second porous membrane 148 facing the intermediate-extractant chamber 152.

In operation, the aqueous feed solution is pumped by the feed-solution pump 160 at a substantially constant rate through the feed-solution chamber 150 and out through the feed-solution discharge throttle valve 162. The intermediate-extractant chamber 152 is filled with an intermediate extractant liquid which is substantially immiscible with the feed solution. The intermediate extractant in the intermediate extractant chamber 152 preferably remains essentially stagnant, although a trickle flow through the chamber may be maintained if the intermediate extractant degenerates with time. The aqueous back-extractant liquid is pumped through the back-extractant chamber 154 at a substantially constant rate by the back-extractant input pump 174 and discharged through the back-extractant discharge throttle valve 178.

In the three-chamber extractant cell of FIG. 4, the water-immiscible intermediate extractant wets the hydrophobic sides 149 and 153 of the first and the second membranes 146 and 148. The aqueous feed solution and the aqueous back extractant respectively wet the hydrophilic sides 147 and 151 of the porous membranes 146 and 148. The interface between the feed solution and the intermediate extractant is essentially immobilized at the first membrane 146. The interface between the intermediate extractant and the back extractant is essentially immobilized at the second membrane 148.

Solute in the feed solution is transferred through the pores of the first porous membrane 146 to the intermediate extractant in the intermediate extractant chamber 152. The solute then diffuses across the intermediate extractant chamber 152 and is transferred through the pores of the second porous membrane 148 to the back-extractant liquid in the back-extractant chamber 154. The solute in the back-extractant chamber 154 is then swept with the back-extractant out the chamber and collected.

Figure 5:
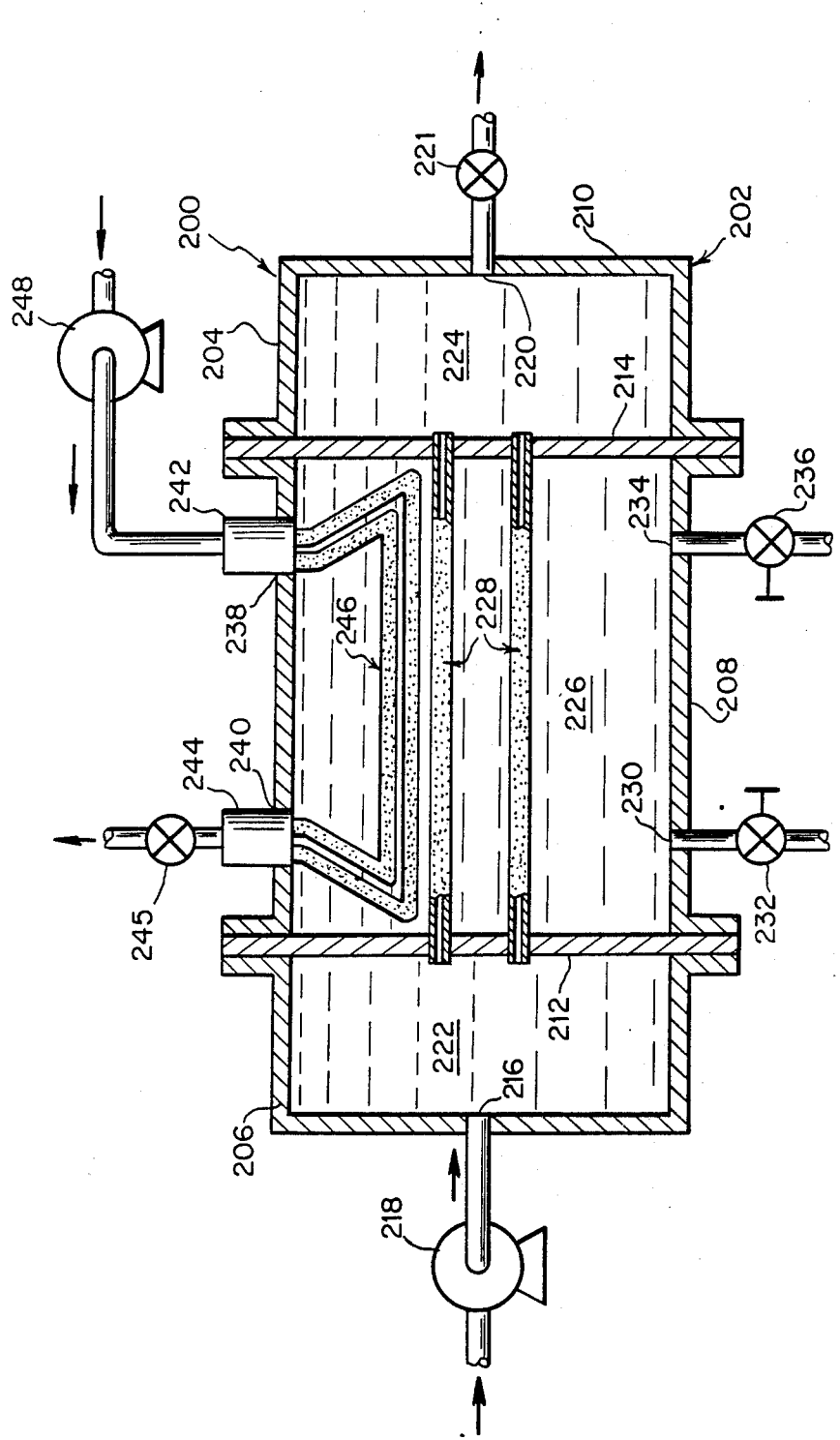
FIG. 5 is a schematic diagram of a third solute-transfer unit which employs hollow fibers of the invention having asymmetrically-wettable, porous walls.

Turning now to FIG. 5, a solute transfer unit 200 includes an extraction cell 202. The extraction cell 202 includes a generally cylindrical pressure vessel 204 which serves as the housing for the extraction cell. The pressure vessel 204 is made up of a feed-solution input section 206, a solute transfer section 208 and a feed-solution output section 210. A feed-solution input partition 212 is located between the feed-solution input section 206 and the solute-transfer section 208. The volume enclosed by the feed solution input section 206 of the pressure vessel 204 and the input partition 212 defines a feed solution input manifold 222. A feed-solution output partition 214 is located between the solute-transfer section 208 and the feed-solution output section 210. The volume enclosed by the feed-solution output section 210 of the pressure vessel 204 and the output partition 214 defines a feed-solution output manifold 224. The volume enclosed by the solute-transfer section 208 of the pressure vessel 204 and the input and output partitions 212 and 214 defines an intermediate extractant chamber 226.

The feed-solution input section 206 of the pressure vessel 204 has a feed solution input port 216 which is connected to a feed solution input pump 218 for pumping a water-immiscible feed solution into the feed solution input manifold 222. The feed solution output section 210 has a feed-solution output port 220 to which a feed-solution discharge throttle valve 221 is connected through which feed solution in the feed solution output manifold 224 can be discharged. A plurality of hollow feed-solution solute transfer tubes 228 extend from the feed-solution input manifold 222 to the feed-solution output manifold 224. The feed solution solute-transfer tubes 228 pass through the input partition 212, extend across the intermediate-extractant chamber 226 and pass through the output bulkhead 214. The solute transfer tubes 228 are embedded in the partitions 212 and 214 by an epoxy adhesive. The hollow solute-transfer fibers 228 have asymmetrically-wettable, porous walls. The fibers are made of hollow porous polypropylene fibers coated on the radially outer surface with porous cellulose acetate. The fibers have a wall thickness of about 50 $\mu$m and an inside diameter of about 0.25 mm.

The solute transfer section 208 of the pressure vessel 204 has an aqueous intermediate extractant inlet port 230 connected to an intermediate-extractant inlet valve 232 for introducing an intermediate-extractant into the intermediate extractant chamber 226. An intermediate extractant outlet port 234 connected to an intermediate outlet valve 236 is provided in the solute-transfer section 208 for discharging intermediate extractant from the intermediate-extractant chamber 226.

The solute transfer section 208 of the pressure vessel 204 has a back-extractant inlet port 238 and a back extractant outlet port 240 passing through it. Connected to the back-extractant inlet port 238 is a back-extractant input manifold housing 242, the interior of which defines a back extractant input manifold (not shown).

A plurality of back-extractant solute-transfer fibers 246 extend from the back-extractant input manifold to the back-extractant output manifold. The back-extractant solute-transfer fibers 146 are made of the same porous cellulose-acetate coated polypropylene fibers as the feed-solution solute-transfer fibers 228. The back-extractant solute-transfer fibers 246 extend through the intermediate-extractant chamber 226 and intermingle with the feed-solution solute transfer fibers 228. The feed-solution solute transfer fibers 228 and the back-extractant solute-transfer fibers 226 are located close to one another to minimize the mean distance the solute must traverse in passing from the one set of tubes to the other.

Commingled bundles of the feed-solution solute-transfer fibers 228 and the back-extractant solute-transfer fibers 246 can be prepared as follows. First, about 500 lengths of hollow tubular fiber are cut to substantially the same length to serve as the feed-solution solute-transfer tubes 228. The lengths of fibers are laid side-by-side on a flat surface. By weaving thread crosswise of the hollow tubular fibers in strips at other end, the fibers are bound together to form a flat mat. A similar mat is prepared with about 500 sections of hollow tubular fibers of a length suitable for the back-extractant solute-transfer fibers 246. The back-extractant solute-transfer fibers 246 are longer than the feed-solution solute transfer fibers 228 in the extraction cell 202. The mat of the fibers for the feed-solution solute-transfer fibers 228 is placed on top of the mat for the back-extractant solute-transfer fibers 246, with the fibers of each mat running essentially in parallel and with the shorter mat centered lengthwise on the longer mat. The two mats are then rolled up to form a cylinder with the fibers running generally parallel to the cylinder axis. The cylinder of fibers is then placed in the solute-transfer section 208 of the extraction cell 202. The woven strip of the shorter mat are then unraveled to free the ends of the shorter fibers. The ends of the longer fibers, which protrude from either end of the cylinder, are gathered into three or four bundles and brought out through the corresponding back-extractant input or output manifold. The four groups of ends of fibers are then potted separately in epoxy. Specifically, the ends are immersed in a layer of liquid epoxy and hardened, which is allowed to cure. The epoxy blocks the openings of most of the hollow fibers. In order to reopen the opening in the fibers, a slice is cut from the epoxy. Depending on the nature of the fibers and the epoxy, the slice may be cut from the epoxy after it has fully cured or when it has only partially cured. The cured epoxy serves on the feed solution input and output partitions 212 and 214.

A back-extractant input pump 248 is connected to the back-extractant input fitting 242 for pumping a water-immiscible back-extractant liquid through the back-extractant solute transfer tubes 246.

In operation, the feed-solution input pump 218 pumps a water-immiscible feed solution at a substantially constant rate into the feed-solution input manifold 222, through the feed-solution solute-transfer fibers 228, and into the feed-solution output manifold 224 where it is discharged through the feed solution discharge throttle valve 221. The back-extractant input pump 248 pumps a water-immiscible back-extractant liquid at a substantially constant rate into the back-extractant input manifold, through the back-extractant solute-transfer tubes 246, and into the back-extractant output manifold, from which it is discharged through the back-extractant discharge throttle valve 245. The intermediate extractant chamber 226 is filled with an aqueous intermediate extractant.

Solute in the feed solution is transferred through the porous walls of the feed solution solute-transfer fibers 228 to the intermediate extractant in the intermediate extractant chamber 226 and thence through the porous walls of the back-extractant solute-transfer fibers 246 to the back extractant flowing in the transfer fibers 246. The back extractant in which the solute is dissolved is collected from the output of the back-extractant discharge throttle valve 245.

EXAMPLES

The following solute-transfer unit was used in the Examples set forth below.

An immobilized-interface extraction cell had a housing consisting of a first and a second generally disk-shaped block of stainless steel. The extraction-cell housing blocks were about 6.4 cm in diameter and about 2.2 cm thick. A generally disk-shaped depression was milled in one face of each block to define a liquid chamber which served as either the extractant chamber or the feed-solution chamber of the extraction cell. The liquid-chamber depressions were approximately 0.25 mm deep and approximately 3.7 cm in diameter.

Each extraction-cell housing block had two channels passing through it to serve as liquid inlet and outlet channels. Each channel consisted of a hole which extended radially inward from a side of the block at approximately the midplane of the block and connecting with seven holes extending axially from the midplane to the base of the liquid-chamber depression. The openings of the seven holes for each channel were disposed along a radius of the disk-shaped liquid-chamber depression from about 0.5 cm from the center of the depression to about 1.6 cm from the center. The radius along which the seven openings of one channel were located extended in generally the opposite direction from the radius along which the seven openings of the other channel were located. The use of seven openings into the liquid-chamber depression permitted liquid to be introduced into and withdrawn from the chamber at linear velocities not substantially higher than the linear velocities of the liquid passing through the chamber.

Two substantially circular grooves for two O-ring seals were cut in the face of the first extraction cell housing block substantially concentric with one another and encircling the liquid-chamber depression in the face. The radially inner groove was about 4.1 cm in diameter and the radially outer groove was about 5.0 cm in diameter.

Porous membranes for the extraction cell were in the form of composite, two-layer disks about 4.8 cm in diameter cut from sheets of porous-membrane material. The diameter of the porous membrane disks was greater than the diameter of the inner O-ring seal but less than the diameter of the outer O-ring seal. The composite two-layer disks were made by clamping together in the extraction cell a first disk of porous cellulose acetate film and a second disk of porous polypropylene film. The cellulose acetate film was about 125 $\mu$m thick, had a porosity of about 0.65 and size of about 0.2 $\mu$m. Such a cellulose acetate film is commercially available from Microfiltraction System of Dublin, Calif. The polypropylene film was about 25 $\mu$m thick, had a porosity of about 0.38 and an average pore size of about 0.02 $\mu$m The polypropylene film is marketed under the tradename "Celgard 2400" by Celanese Corporation of Summit, N.J.

A circular disk of porous stainless-steel screening about 3.7 cm in diameter and about 0.3 mm thick was cut from a sheet of screening available under the tradename "Rigimesh, Grade Z" from Pall and Trinity Corporation of Cortland, N.Y. The disk of screening was just large enough to fit within a depression on the face of a housing block. The disk of screening provided mechanical support for the porous membrane.

The extraction cell was assembled by placing O-ring seals in the O-ring seal grooves of the first extraction cell housing block and placing the disk of screening in the liquid-chamber depression in the face of the second housing block. The porous membrane disk was placed over the mouth of the depression on the second housing block on top of the disk of screening in substantially coaxial alignment with the depression. The two extraction cell housing blocks were then clamped together in substantially coaxial alignment with the faces of the blocks having liquid-chamber depressions facing one another. The radially inner O-ring seal held the porous membrane disk in place, and the radially outer O-ring seal formed a liquid-tight seal between the two housing blocks.

The two housing blocks were oriented azimuthally relative to one another so that an inlet to the liquid chamber of the first housing block was substantially aligned with an outlet of the liquid chamber in the second housing block, and an outlet to the liquid chamber of the first housing block was substantially aligned with an inlet of the liquid chamber in the second housing block. Consequently, liquid flowing from the inlet to the outlet in the two liquid chambers flowed in generally opposing directions to one another.

Two stainless-steel pressure vessels served as reservoirs for the feed solution and the extractant, respectively. Each pressure vessel was connected to an inlet port of one of the liquid chambers of the extractant cell via a pressure line. An adjustable throttle valve was connected to the outlet port for each liquid chamber. A source of compressed nitrogen was connected to each pressure vessel across a pressure regulating valve for pressurizing the contents of the pressure vessel to the pressure set by the valve. Pressurizing liquid contained in a pressure vessel to a value above ambient atmospheric pressure caused it to flow under pressure through the liquid chamber connected to the pressure vessel and then from the liquid chamber through the throttle valve to be discharged. The throttle valve would be adjusted so that the resistance to flow imposed by the valve was substantially greater than the resistance to flow in the liquid path from the pressure vessel to the throttle valve. Consequently, the throttle valve could be set so that essentially all of the pressure drop between the pressure in the pressure vessel and the ambient atmospheric pressure at the discharge outlet of the throttle valve occurred across the throttle valve. In that case, the pressure in the liquid chamber was substantially the same as the pressure impressed on the liquid in the pressure vessel by the compressed nitrogen. Thus, if the pressure in one pressure vessel differed from the pressure in the second pressure vessel by a selected amount, the pressure in the two fluid chambers connected respectively to the two pressure vessels differed by essentially the same amount.

The disk of screening in the liquid-chamber depression in the face of the second housing block supported the porous membrane clamped between the two housing blocks against a pressure difference directed from the liquid chamber in the first housing block to the fluid chamber in the second housing block. In other words, the screening supported the porous membrane if the pressure in the fluid chamber adjacent to the side of the porous membrane against which the screening was located was less than the pressure on the opposite side of the membrane.

EXAMPLE 1

A feed solution of acetic acid in water was prepared from reagent grade glacial acetic acid and distilled water. The concentration of acetic acid in the feed solution was found to be about $4.2 \times 10^{-4}$ gmol/ml by titrating an aliquot of the solution with a standard NaOH solution.

The composite disk of porous cellulose acetate and porous polypropylene was mounted between the two extraction-cell housing blocks. Specifically, the disk of porous cellulose acetate and the disk of porous polypropylene were placed face-to-face and mounted between the two extraction-cell housing blocks with the porous cellulose acetate facing the first extraction-cell housing block and the porous polypropylene disk resting against the disk of screening and facing the second extraction-cell housing block. The pressure vessel connected to the second extraction-cell housing block was charged with pure xylene of ACS grade. The pressure vessel connected to the first housing block was charged with the aqueous acetic acid feed solution.

The pressure vessel charged with xylene was then pressurized to a pressure just slightly above ambient atmospheric pressure. The throttle valve connected to the outlet of the second housing block was adjusted so that the volume flow rate of xylene through the extraction cell was about 54 cm$^3$/min.

The pressure vessel charged with the aqueous acetic acid feed solution was then charged to a pressure of about 97 kPa above ambient atmospheric pressure. The throttle valve connected to the outlet of the first extraction-cell housing block was adjusted so that the volume flow rate of the aqueous acetic acid feed solution through the extraction cell was about 17 cm$^3$/min.

Both the aqueous feed solution and the xylene were about 25° C. upon passing through the extraction cell.

No organic liquid was observed in the aqueous solution discharged from the extraction cell and no aqueous liquid was observed in the xylene phase discharged from the cell.

An aliquot of the xylene phase discharged from the extraction cell was collected after the steady state was reached and analyzed for acetic acid content by titrating with a standard NaOH solution. The xylene was found to contain about $0.15 \times 10^{-6}$ gmol/ml acetic acid.

For comparison, if equal volumes of the aqueous acetic acid feed solution and xylene were mixed together and allowed to equilibrate at 25° C., the xylene phase would be expected to contain about $6.6 \times 10^{-6}$ gmol/ml of acetic acid at equilibrium. This equilibrium concentration of acetic acid in xylene was calculated using a distribution coefficient of about 0.012 measured for acetic acid in water and xylene at about 25° C. over a concentration range of acetic acid in xylene which includes the concentration calculated here.

After the steady state conditions have been reached in the extraction cell, the quantity of acetic acid transferred across a unit area of the porous membrane from the aqueous feed solution to the xylene solution per unit time can be measured by collecting the xylene solution discharged from the cell for a given length of time, analyzing the solution collected for total acetic acid content, and dividing the quantity of acetic acid so found by the collection time and by the area of the porous membrane accessible to the feed solution and the xylene. The resulting value for the rate of solute transfer, denoted W, has the units gmol acetic acid/cm$^2$ sec. The rate of solute transfer W can be related to a transfer coefficient $K_o$, which characterizes the porous membrane of the extraction cell. Specifically, the transfer coefficient $K_o$ is defined by the equation $$W = K_o A (mC_{fs} - C_e)$$

where:

W is the rate of solute transfer defined above;
A is the area of the porous membrane contacted by the feed solution and extractant in the extraction cell. In the present extraction cell, the area A has a value of 13.37 cm$^2$;
m is the equilibrium distribution coefficient of acetic acid in water and xylene at the concentration of acetic acid in water discharged from the extraction cell and at the temperature of the extraction;
$C_{fs}$ is the concentration of acetic acid in the aqueous feed solution at the inlet to the extraction cell; and $C_e$ is the concentration of the acetic acid in the xylene discharged from the extraction cell. In the present example, the transfer coefficient $K_o$ was found to be about $18.2 \times 10^{-4}$ cm/sec.

EXAMPLE 2

The procedure of Example 1 was repeated with the following differences. The composite porous membrane was reversed in orientation so that the porous cellulose acetate disk rested against the disk of screening. The pressure vessel connected to the second extraction-cell housing block—which contained the disk of screening—was charged with the aqueous acetic acid feed solution. The pressure vessel connected to the first housing block was charged with pure xylene.

The pressure vessel charged with xylene was pressurized to a pressure of about 97 kPa above ambient atmospheric pressure. The throttle valve connected to the outlet of the first housing block was adjusted so that the volume flow rate of xylene through the extraction cell was about 41 cm³/min.

The pressure vessel charged with the aqueous acetic acid feed solution was pressurized to a pressure above ambient atmospheric pressure just great enough to cause a flow rate of about 17 cm³/min through the extraction cell with the throttle valve connected to the second housing block essentially fully open.

No droplets of a xylene phase were observed in the aqueous solution discharged from the extraction cell and no droplets of a water phase were observed in the xylene solution discharged from the extraction cell.

The concentration of acetic acid in the xylene discharged from the extraction cell after a steady state was reached was found to be about $0.17 \times 10^{-6}$ gmol/ml. The solute transfer coefficient $K_o$ for the membrane was about $17.6 \times 10^{-4}$ cm/sec.

EXAMPLE 3

The procedure of Example 1 was repeated with the exceptions noted below.

The flow rate of xylene through the extraction cell was about 84 cm³/min. The flow rate of the aqueous feed solution was about 18 cm³/min. The pressure of both the xylene and the aqueous acetic acid was about 29 kPa above ambient atmospheric pressure.

No droplets of a xylene phase were observed in the aqueous solution discharged from the extraction cell and no droplets of an aqueous phase were observed in the xylene solution discharged from the extraction cell.

The concentration of acetic acid in the xylene discharged from the extraction cell after a steady state was reached was found to be about $0.10 \times 10^{-6}$ gmol/ml. The solute transfer coefficient $K_o$ was about $18.3 \times 10^{-4}$ cm/sec of 25° C.

EXAMPLE 4

The procedure of Example 1 was repeated with the following exceptions.

The volume flow rate of the xylene through the extraction cell was about 60 cm³/min. The volume flow rate of the aqueous feed solution through the extraction cell was about 18 cm³/min. The pressure on both the feed solution and the xylene was about 97 kPa above ambient atmospheric pressure.

No droplets of a xylene phase were observed in the aqueous solution discharged from the extraction cell and no droplets of a water phase were observed in the xylene solution discharged from the extraction cell.

The concentration of acetic acid in the xylene solution discharged from the extraction cell after a steady state was achieved was found to be about $0.13 \times 10^{-6}$ gmol/ml. The solute transfer coefficient $K_o$ was found to be about $18.7 \times 10^{-4}$ cm/sec.

It is not intended to limit the present invention to the specific embodiments disclosed above. It is recognized that changes may be made in the processes and apparatus specifically described herein without departing from the scope and teachings of the instant invention. For example, the process of the invention is not limited to immiscible aqueous-organic extraction systems. Polar organic solvents such as ethylene glycol, sulfolane, dimethyl sulfoxide, n-methyl pyrrolidone or propylene carbonate may be used to contact the hydrophilic side of an asymmetrically-wettable, porous membrane of the invention while a hydrocarbon mixture contacts the hydrophobic side. Aromatic compounds may be transferred from one of these liquids to the other through the membrane. It is intended to encompass all other embodiments, alternatives and modifications consistent with the present invention.

I claim:

1. A process for transferring solute from a liquid feed solution to a liquid extractant, the feed solution and the extractant being substantially immiscible when in direct contact with each other, one of the feed solution and the extractant being substantially miscible with water to define a water-miscible liquid, the other of the feed solution and the extractant being substantially immiscible with water to define a water-immiscible liquid, the process comprising the steps of:
   (a) contacting a first side of an asymmetrically-wettable, porous membrane with the water-miscible liquid, the first side being hydrophilic, the membrane having a second side opposing the first side, the second side being hydrophobic, the membrane having pores which pass through the membrane providing liquid-phase communication between the first side and the second side; and
   (b) contacting the second side of the membrane with the water-immiscible liquid so that the feed solution and the extractant can come into liquid/liquid interfacial contact through the pores of the membrane, the interface between the feed solution and the extractant being substantially immobilized at the porous membrane.

2. The process according to claim 1 in which the feed solution is an aqueous liquid and the extractant is substantially immiscible with water.

3. The process according to claim 1 in which the extractant is an aqueous liquid and the feed solution is substantially immiscible with water.

4. The process according to claim 1 in which the step of contacting the first side of the porous membrane with the water-miscible liquid includes causing a stream of the water-miscible liquid to flow along the first side.

5. The process according to claim 4 in which the step of contacting the second side of the porous membrane with the water-immiscible liquid includes causing a stream of the water-immiscible liquid to flow along the second side.

6. The process according to claim 5 in which the stream of water-miscible liquid and the stream of water-immiscible liquid flow in generally opposing directions so that the transfer of solute from the stream of feed solution to the stream of extractant is a countercurrent process.

7. The process according to claim 1 in which the water-miscible liquid is a polar organic solvent.

8. The process according to claim 1 in which the feed solution is an aqueous fermentation broth.

9. The process according to claim 8 in which the asymmetrically-wettable, porous membrane includes a layer of a porous hydrophilic material, a side of the layer of the porous hydrophilic material defining the first side of the membrane, the porous hydrophilic material contacting the aqueous fermentation broth.

10. The process according to claim 9 in which fermentation cells are immobilized in the layer of porous hydrophilic material of the membrane.

11. The process according to claim 9 in which enzymes are immobilized in the layer of porous hydrophilic material of the membrane.

* * * * *